(12) United States Patent
Hommann et al.

(10) Patent No.: US 11,426,529 B2
(45) Date of Patent: Aug. 30, 2022

(54) AUTO-INJECTOR WITH ACTIVE AGENT CONTAINER LATCHING

(71) Applicant: Ypsomed AG, Burgdorf (CH)

(72) Inventors: Edgar Hommann, Grossaffoltern (CH); Benjamin Scherer, Uster (CH)

(73) Assignee: Ypsomed AG, Burgdorf (CH)

( * ) Notice: Subject to any disclaimer, the term of this patent is extended or adjusted under 35 U.S.C. 154(b) by 0 days.

(21) Appl. No.: 17/191,127

(22) Filed: Mar. 3, 2021

(65) Prior Publication Data
US 2021/0236733 A1 Aug. 5, 2021

Related U.S. Application Data

(63) Continuation of application No. 16/658,378, filed on Oct. 21, 2019, now Pat. No. 10,973,988, which is a
(Continued)

(30) Foreign Application Priority Data

Dec. 18, 2003 (CH) ..................................... 2186/03

(51) Int. Cl.
*A61M 5/32* (2006.01)
*A61M 5/20* (2006.01)
*A61M 5/31* (2006.01)

(52) U.S. Cl.
CPC ........ *A61M 5/3202* (2013.01); *A61M 5/2033* (2013.01); *A61M 5/326* (2013.01);
(Continued)

(58) Field of Classification Search
CPC .............. A61M 5/2033; A61M 5/3202; A61M 5/3204; A61M 5/20; A61M 5/3243;
(Continued)

(56) References Cited

U.S. PATENT DOCUMENTS

| | | |
|---|---|---|
| 2,221,739 A | 11/1940 | David |
| 4,378,015 A | 3/1983 | Wardlaw |

(Continued)

FOREIGN PATENT DOCUMENTS

| | | |
|---|---|---|
| DE | 289412 A7 | 5/1991 |
| DE | 10320225 A1 | 12/2004 |

(Continued)

OTHER PUBLICATIONS

German Federal Patent Court register information in regards to nullification proceedings against DE 102004060146.1 C5 (which claims priority to the same priority application as the instant application CH 2186/03), the proceedings made available on the public register as of Feb. 8, 2021, 2 pages.

*Primary Examiner* — Nilay J Shah
(74) *Attorney, Agent, or Firm* — Dorsey & Whitney LLP

(57) ABSTRACT

In an elongated casing, an active agent container connected to an injection needle can be shifted axially by a spring force. Auto-injectors distributed pre-filled and with the springs tensed may be provided with a needle protecting cap to ensure sterility of the needle. When the needle protecting cap is removed as preparation for using the auto-injector, a tensile force can be exerted on the active agent container. Therefore, the active agent container and needle must be prevented from being undesirably pulled forwards. At least one latching tongue prevents the active agent container from being prematurely shifted with respect to the casing, by abutting a flange arranged on a sliding sleeve accommodating the active agent container. When the auto-injector is placed onto the skin, a needle protecting tube is shifted into the casing, forcing the latching tongue away from the flange, thereby freeing the travel path for needle movement.

19 Claims, 6 Drawing Sheets

Related U.S. Application Data continuation of application No. 15/825,828, filed on Nov. 29, 2017, now Pat. No. 10,493,213, which is a continuation of application No. 15/248,192, filed on Aug. 26, 2016, now Pat. No. 9,855,392, which is a continuation of application No. 14/579,064, filed on Dec. 22, 2014, now Pat. No. 9,427,528, which is a continuation of application No. 13/854,425, filed on Apr. 1, 2013, now Pat. No. 8,945,049, which is a continuation of application No. 11/836,503, filed on Aug. 9, 2007, now Pat. No. 8,409,149, which is a continuation of application No. 11/016,539, filed on Dec. 17, 2004, now Pat. No. 7,357,790.

(52) U.S. Cl.
CPC .............. *A61M 2005/206* (2013.01); *A61M 2005/2013* (2013.01); *A61M 2005/2073* (2013.01); *A61M 2005/3118* (2013.01); *A61M 2005/3247* (2013.01); *A61M 2205/273* (2013.01)

(58) Field of Classification Search
CPC ........ A61M 5/31571; A61M 2005/206; A61M 2005/2073; A61M 2005/2013; A61M 2005/3247
See application file for complete search history.

(56) References Cited

U.S. PATENT DOCUMENTS

| | | | |
|---|---|---|---|
| 4,487,602 A | | 12/1984 | Christensen et al. |
| 4,693,708 A | * | 9/1987 | Wanderer ............... A61B 5/153 604/198 |
| 4,801,295 A | | 1/1989 | Spencer |
| 4,894,055 A | | 1/1990 | Sudnak |
| 4,902,279 A | | 2/1990 | Schmidtz et al. |
| 5,137,516 A | * | 8/1992 | Rand .................... A61M 5/2033 604/136 |
| 5,176,643 A | | 1/1993 | Kramer et al. |
| 5,271,744 A | | 12/1993 | Kramer et al. |
| 5,478,316 A | * | 12/1995 | Bitdinger ............ A61M 5/2033 604/135 |
| 5,536,249 A | * | 7/1996 | Castellano ............. G16H 20/17 604/65 |
| 5,609,577 A | | 3/1997 | Haber et al. |
| 5,637,094 A | | 6/1997 | Stewart, Jr. et al. |
| 5,658,259 A | | 8/1997 | Pearson et al. |
| 5,681,291 A | * | 10/1997 | Galli .................... A61M 5/2033 604/156 |
| 6,099,503 A | | 8/2000 | Stradella |
| 6,258,068 B1 | | 7/2001 | Kirchhofer et al. |
| 6,270,479 B1 | | 8/2001 | Bergens et al. |
| 6,280,421 B1 | | 8/2001 | Kirchhofer et al. |
| 6,544,234 B1 | | 4/2003 | Gabriel |
| 6,575,939 B1 | | 6/2003 | Brunel |
| 6,620,137 B2 | | 9/2003 | Kirchhofer et al. |
| 6,767,336 B1 | | 7/2004 | Kaplan |
| 6,773,415 B2 | | 8/2004 | Heiniger |
| 7,004,929 B2 | | 2/2006 | Mcwethy et al. |
| 7,074,211 B1 | | 7/2006 | Heiniger et al. |
| 7,128,728 B2 | | 10/2006 | Kirchhofer et al. |
| 7,252,651 B2 | | 8/2007 | Haider et al. |
| 7,357,790 B2 | | 4/2008 | Hommann et al. |
| 7,361,160 B2 | | 4/2008 | Hommann et al. |
| 7,695,453 B2 | | 4/2010 | Marshall et al. |
| 8,409,149 B2 | | 4/2013 | Hommann et al. |
| 8,945,049 B2 | | 2/2015 | Hommann et al. |
| 9,427,528 B2 | | 8/2016 | Hommann et al. |
| 9,855,392 B2 | | 1/2018 | Hommann et al. |
| 10,493,213 B2 | | 12/2019 | Hommann et al. |
| 2001/0037087 A1 | | 11/2001 | Knauer |
| 2003/0036725 A1 | | 2/2003 | Lavi et al. |
| 2003/0105430 A1 | * | 6/2003 | Lavi .................... A61M 5/2033 604/136 |
| 2004/0025262 A1 | | 2/2004 | Hamers et al. |
| 2004/0039336 A1 | | 2/2004 | Amark et al. |
| 2004/0225262 A1 | | 11/2004 | Fathallah et al. |
| 2005/0049561 A1 | | 3/2005 | Hommann et al. |
| 2005/0101919 A1 | | 5/2005 | Brunnberg |
| 2005/0203466 A1 | | 9/2005 | Hommann et al. |
| 2005/0261634 A1 | | 11/2005 | Karlsson |
| 2006/0189938 A1 | | 8/2006 | Hommann et al. |
| 2007/0021720 A1 | | 1/2007 | Guillermo |
| 2008/0015520 A1 | | 1/2008 | Hommann et al. |
| 2008/0147006 A1 | | 6/2008 | Brunnberg et al. |
| 2008/0262436 A1 | | 10/2008 | Olson |
| 2009/0005735 A1 | | 1/2009 | Wikner et al. |
| 2013/0218094 A1 | | 8/2013 | Hommann et al. |
| 2015/0112273 A1 | | 4/2015 | Hommann et al. |
| 2016/0361502 A1 | | 12/2016 | Hommann et al. |
| 2018/0078713 A1 | | 3/2018 | Hommann et al. |
| 2020/0046909 A1 | | 2/2020 | Hommann et al. |
| 2020/0297930 A1 | | 9/2020 | Hommann et al. |
| 2020/0338274 A1 | | 10/2020 | Hommann et al. |

FOREIGN PATENT DOCUMENTS

| | | |
|---|---|---|
| DE | 202004016791 U1 | 12/2004 |
| DE | 102004060146 A1 | 8/2005 |
| EP | 0577448 A1 | 1/1994 |
| EP | 0666084 A2 | 8/1995 |
| EP | 1932558 A1 | 6/2008 |
| WO | 9421316 A1 | 9/1994 |
| WO | 0247746 A1 | 6/2002 |
| WO | 2005023341 A1 | 3/2005 |
| WO | 2005035029 A1 | 4/2005 |
| WO | 2005044344 A1 | 5/2005 |
| WO | 2005044347 A1 | 5/2005 |
| WO | 2005115507 A1 | 12/2005 |
| WO | 2006057604 A1 | 6/2006 |
| WO | 2006129196 A1 | 7/2006 |

* cited by examiner

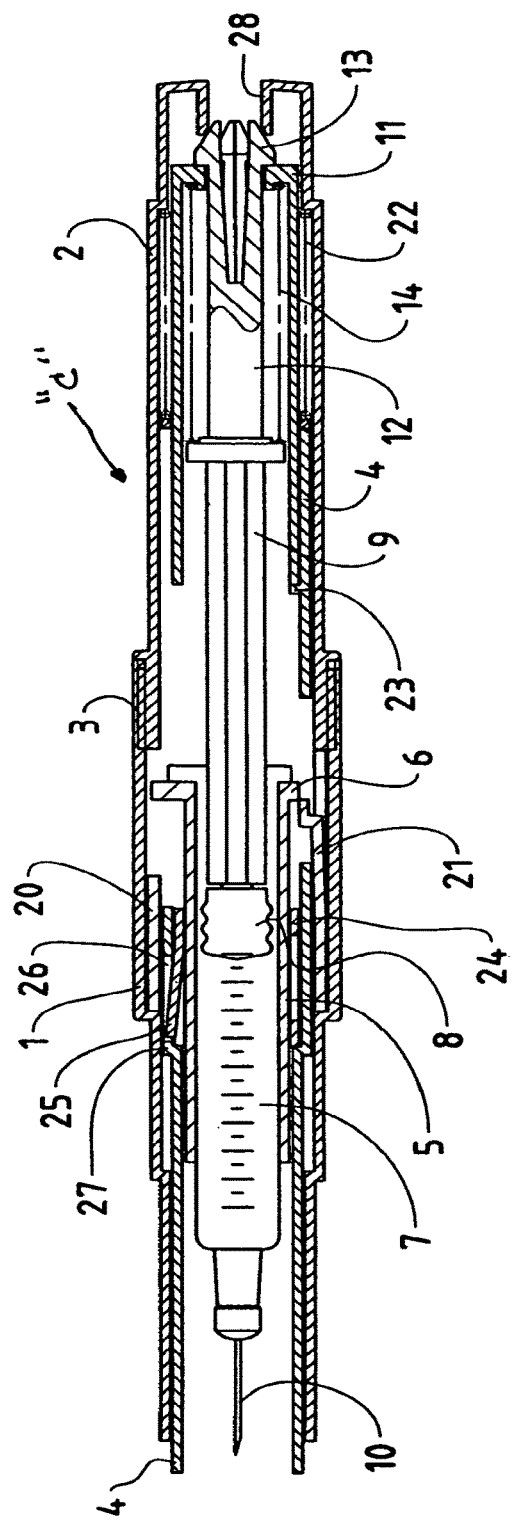
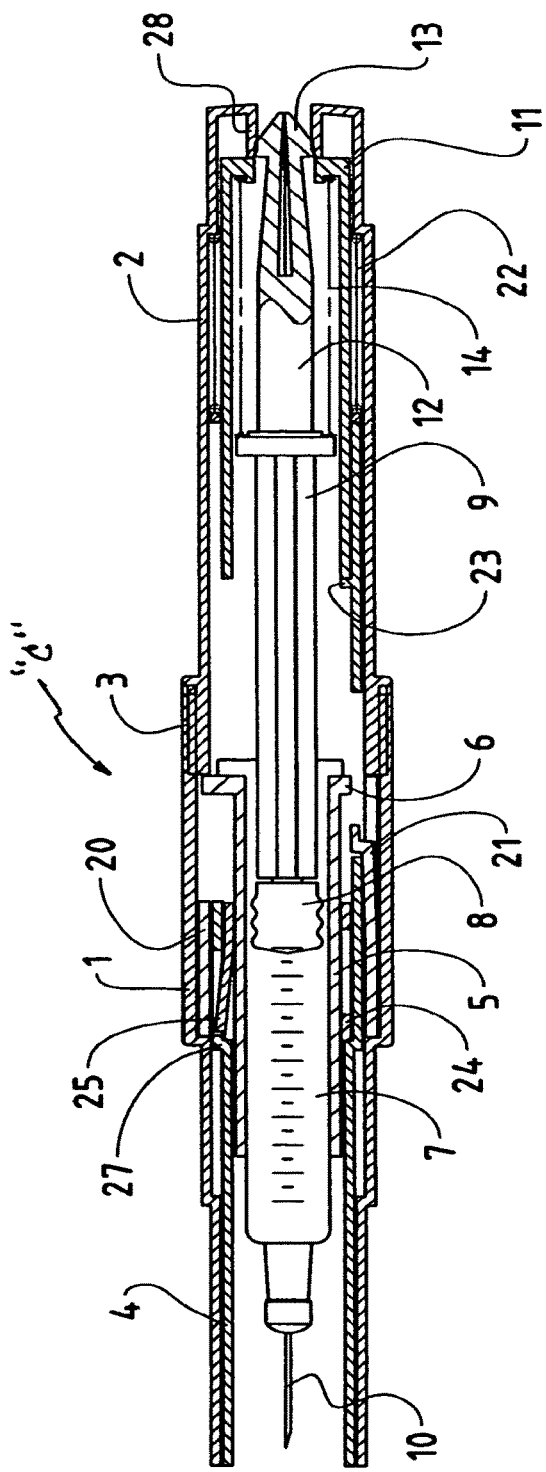
FIG. 3
FIG. 4

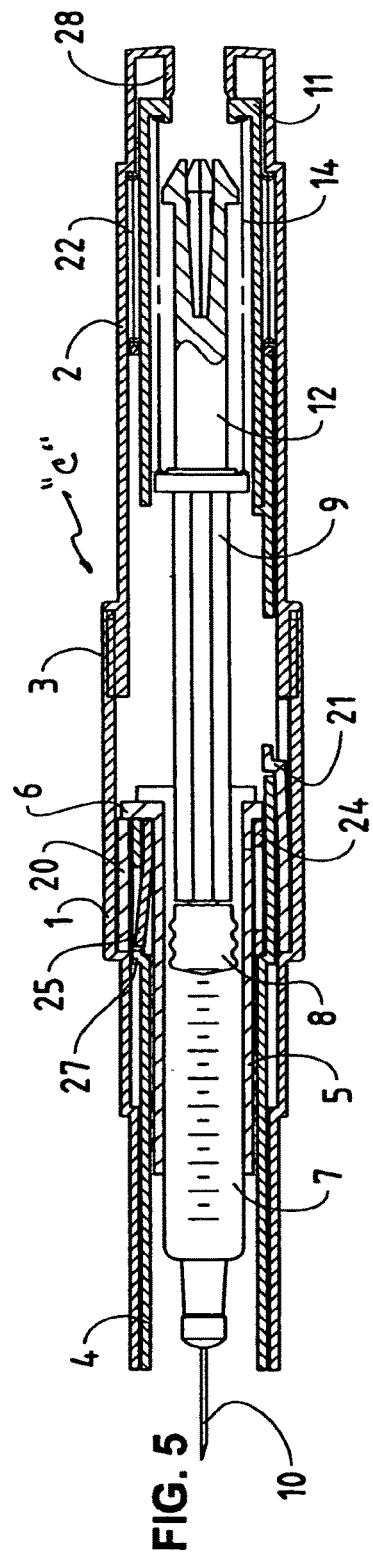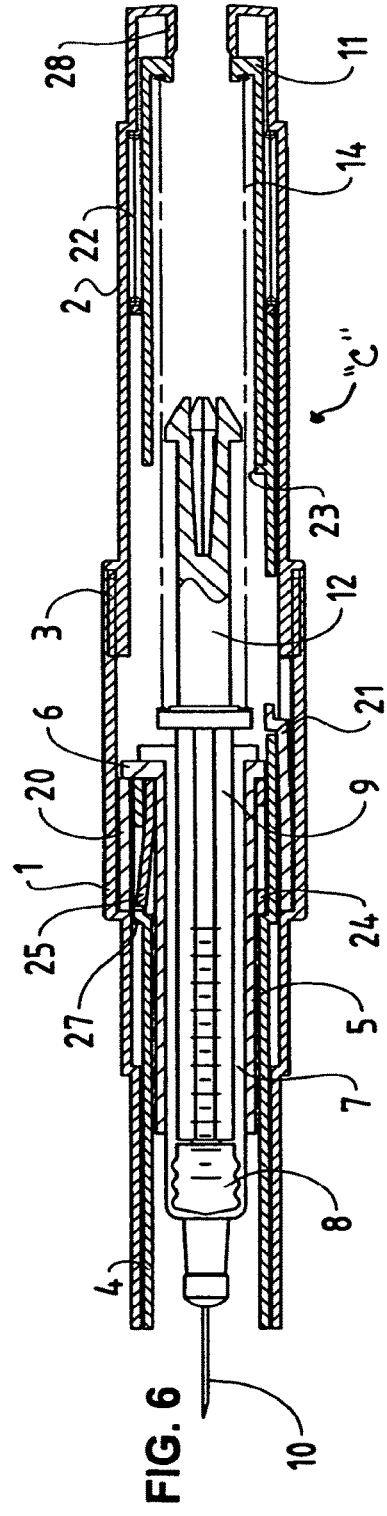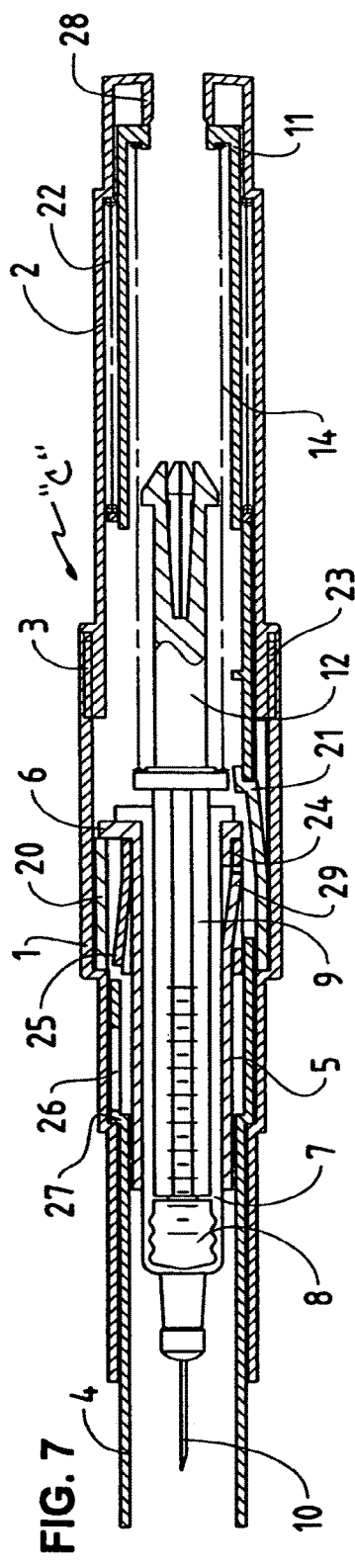

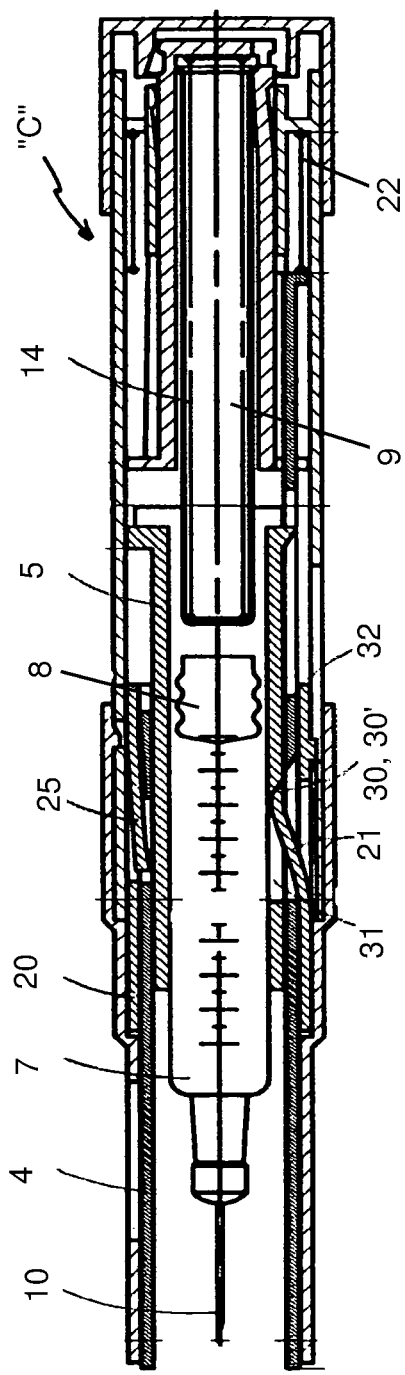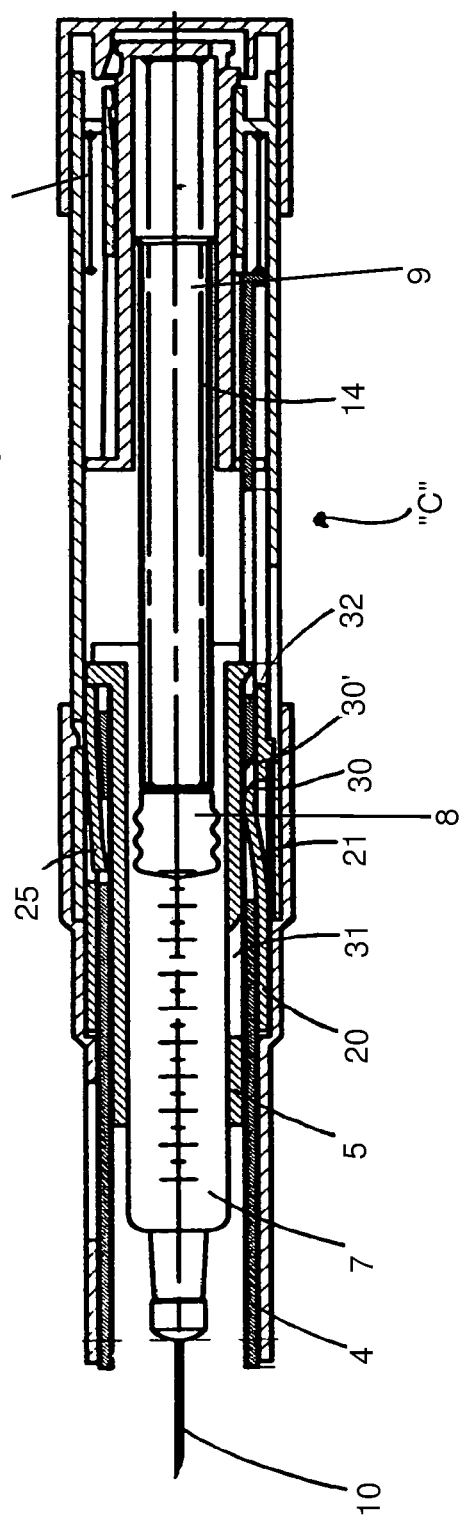

AUTO-INJECTOR WITH ACTIVE AGENT CONTAINER LATCHING

CROSS-REFERENCE TO RELATED APPLICATIONS

This application is a continuation of U.S. application Ser. No. 16/658,378, filed Oct. 21, 2019 and issued as U.S. Pat. No. 10,973,988 on Apr. 13, 2021, which is a continuation of U.S. application Ser. No. 15/825,828, filed Nov. 29, 2017, and issued as U.S. Pat. No. 10,493,213 on Dec. 3, 2019, which is a continuation of U.S. application Ser. No. 15/248,192 filed Aug. 26, 2016, and issued as U.S. Pat. No. 9,855,392 on Jan. 2, 2018, which is a continuation of U.S. application Ser. No. 14/579,064 filed Dec. 22, 2014 and issued as U.S. Pat. No. 9,427,528 on Aug. 30, 2016, which is a continuation of U.S. application Ser. No. 13/854,425 filed Apr. 1, 2013 and issued as U.S. Pat. No. 8,945,049 on Feb. 3, 2015, which is a continuation of U.S. application Ser. No. 11/836,503 filed on Aug. 9, 2007 and issued as U.S. Pat. No. 8,409,149 on Apr. 2, 2013, which is a continuation of U.S. application Ser. No. 11/016,539 filed on Dec. 17, 2004 and issued as U.S. Pat. No. 7,357,790 on Apr. 15, 2008, which claims priority to Swiss application No. CH 2186/03, filed on Dec. 18, 2003, the entire contents of all of which are incorporated by reference herein in their entirety.

BACKGROUND

The invention relates to devices and methods for the administration or delivery of substances, including the administration of medicinal substances to patients. More particularly, it relates to injection or infusion devices and methods, and to an auto-injector for automatically injecting an active agent. In one embodiment, the auto-injector comprises an elongated casing, an injection needle which can be shifted axially in the casing and is connected to an active agent container, a piston which can be shifted in the active agent container for the purpose of delivering the active agent, and a needle protecting tube which can be shifted relative to the casing.

Auto-injectors are known in many different embodiments. They serve to administer injections, in particular by a patient him or herself. When used, an injection needle is automatically inserted, in the majority of cases by means of a spring force, and then an active agent is injected. Many reusable auto-injectors are known and also those which, once used, are partially or completely thrown away. Auto-injectors which are sold or distributed filled and with the springs tensed have to be provided with a needle protecting cap in order to be able to ensure the sterility of the injection needle. Since this needle protecting cap preferably encloses the active agent container connected to the injection needle, forming a seal, a certain tensile force is necessarily exerted on the active agent container as the needle protecting cap is removed in preparation for using the auto-injector.

SUMMARY

In one embodiment, the present invention addresses the object of preventing an active agent container, comprising an injection needle, from being undesirably moved, e.g., pulled forward, for example when removing a needle protecting cap.

This object is addressed in accordance with one embodiment of the invention by providing an injection device with a latching member that, in a latching position, prevents the active agent container from being shifted with respect to the casing of the device, and by providing that the latching member can be moved to a release position, in which it allows the active agent container to be shifted with respect to the casing, by shifting a needle protecting tube into the casing. In one embodiment, the latching member is preferably fixed and/or locked in the latching position by the needle protecting tube.

In one embodiment, the present invention comprises an automatic injection device comprising an elongated casing, and an active agent container connected to an injection needle, wherein the container can be shifted axially by a spring force. Such auto-injectors which are sold or distributed filled and with the springs tensed have to be provided with a needle protecting cap to ensure the sterility of the injection needle. When such a needle protecting cap is removed as preparation for using the auto-injector, a tensile force can be exerted on the active agent container. Therefore, the active agent container comprising the injection needle should be prevented from being undesirably pulled forwards. At least one latching tongue prevents the active agent container from being prematurely shifted with respect to the casing, by abutting a flange arranged on a sliding sleeve which accommodates the active agent container. When the auto-injector is placed onto a person's skin, a needle protecting tube is shifted into the casing, forcing the latching tongue away from the flange and, thus, freeing the travel path for needle movement.

The present invention not only has the advantage that the active agent container remains in position in the auto-injector when the needle protecting cap is removed, but also that the auto-injector is prevented from being intentionally or unintentionally triggered until the needle protecting tube has been shifted into the casing.

In accordance with a preferred embodiment of the invention, the latching member is formed as at least one elastically flexible latching tongue. The tongue can be arranged on the casing itself or, in some preferred embodiments, on a latching sleeve mounted in the casing and formed integrally with the latching sleeve. These measures make it easier to manufacture the components from plastic in an injection moulding process, but alternatives exist, including forming the tongue and sleeve separately and then operably coupling them.

In one embodiment, the latching member preferably prevents the active agent container from being shifted with respect to the casing by abutting a flange arranged on a sliding sleeve which accommodates the active agent container. As it is shifted into the casing, the needle protecting tube forces the latching member away from said flange. This design is simple and operationally reliable.

In accordance with another preferred embodiment of the invention, the latching member comprises a surface which runs or extends obliquely with respect to the longitudinal axis of the auto-injector and abuts a surface, likewise running or extending obliquely with respect to the longitudinal axis of the auto-injector, on the sliding sleeve which accommodates the active agent container. In some embodiments, the oblique surfaces of the latching member and the sliding sleeve ideally run parallel to each other. In some preferred embodiments, the oblique surfaces are each arranged on facing sides of the latching member and the sliding sleeve, such that the tip of the oblique surface of the latching member is provided on a surface of a latching sleeve, the surface pointing outwards from the auto-injector.

In the latching position, the oblique surfaces abut each other and the latching member is held in this position by the needle protecting tube. When the needle protecting tube is shifted into the casing, the latch is released. As soon as pressure is exerted on the sliding sleeve, so as to advance the active agent container comprising the needle for injecting, the oblique surface of the latching member slides outwardly along the oblique surface of the sliding sleeve, such that the sliding sleeve can be advanced. The latching member is therefore moved or forced out of the latching position by the sliding sleeve.

In accordance with another embodiment of the invention, a needle protecting cap is provided which preferably fulfils a double function in that it prevents the needle protecting tube from retracting into the casing when it is placed on the auto-injector. To this end, the needle protecting cap preferably comprises an inner sleeve reaching over the active agent container and an outer sleeve reaching over the needle protecting tube.

BRIEF DESCRIPTION OF THE DRAWINGS (Each of the first seven figures depicts a longitudinal section through one embodiment of an auto-injector in accordance with the present invention, wherein a different operational state is depicted in each figure).

FIG. 3 depicts the state in which the auto-injector is placed on the point of injection;

FIG. 4 depicts triggering;

FIG. 5 depicts the end of injecting;

FIG. 6 depicts the end of delivering the active agent;

FIG. 7 depicts the state once used;

FIG. 9 depicts the auto-injector embodiment of FIG. 8 in a releasing position;

FIG. 10 depicts the auto-injector embodiment of FIG. 8 in a position in which the needle has been injected.

DETAILED DESCRIPTION

Figure 1:
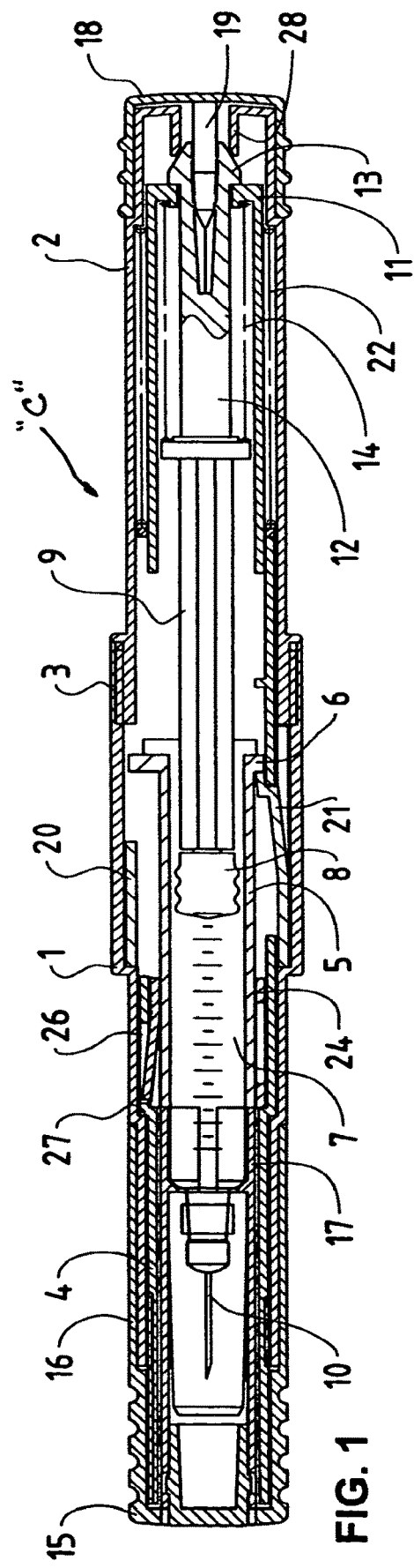
FIG. 1 depicts the condition on delivery.

The drawings depicts one exemplary embodiment of an auto-injector in accordance with the present invention. The depicted auto-injector has a casing "C" comprised of a front casing part 1 and a rear casing part 2, wherein the two casing parts are joined together by a connection 3. If the auto-injector is a refillable auto-injector, the connection 3 is releasable, for example, it may comprise a threaded connection. If, however, the auto-injector is a disposable, the connection 3 can be fixed, for example, by a fused connection, adhesive connection or latching connection. On the left in the figures, a needle protecting tube 4 can be seen which can be shifted axially in the front casing part 1, as will be described in more detail below. A sliding sleeve 5 which can be shifted axially is guided in the needle protecting tube 4 via its front end and in the front casing part 1 via a flange 6 formed on its rear end. The sliding sleeve 5 accommodates an ampoule-like active agent container 7, in the interior of which a piston 8 can be shifted axially with the aid of a piston rod 9, for the purpose of delivering the active agent. At its front end, the active agent container 7 is provided with an injection needle 10.

A locking member in the form of a locking sleeve 24 is mounted externally on the sliding sleeve 5. At least one locking tongue 25 protrudes elastically outwards from the locking sleeve 24 and in the operational state in accordance with FIG. 1 abuts an inner heel 27 of the needle protecting tube 4. A cavity 26 which is formed in the needle protecting tube 4 and into which the locking tongue 25 protrudes is connected to the heel 27. The function of the locking sleeve 24 and the locking tongue 25 will be set forth further below.

A guiding sleeve 11 is arranged in the rear casing part 2, such that it can be shifted axially. A driving part 12, which protrudes backwards out of the guiding sleeve 11 and abuts an end flange of the guiding sleeve 11 via latching projections 13, is situated in the guiding sleeve 11. The driving part 12 contacts the piston rod 9 and is biased against it by a driving spring 14.

In FIG. 1, the auto-injector is depicted in its latched position. This position is useful for the delivery, shipment, sale or storage of the auto-injector since it secured against being intentionally or unintentionally activated and is protected from contamination. A needle protecting cap 15 on the side of the injection needle 10 serves this purpose and has an outer sleeve 16 reaching over the front casing part 1 and the needle protecting tube 4 and an inner sleeve 17 reaching over the injection needle 10 and the front end of the active agent container 7 which encloses it, forming a seal, and thus ensures that the injection needle 10 is clean and sterile. In addition, the attached needle protecting cap 15 also secures the auto-injector against being intentionally or unintentionally triggered, by preventing the needle protecting tube 4 from being touched or shifted.

A securing cap 18, which comprises a securing pin 19 in its centre, is placed on the rear end of the auto-injector, on the right in the figures. The securing pin 19 protrudes between the latching projections 13 of the driving part and thus reliably prevents an injection from being triggered. In order to prepare the auto-injector for use, the needle protecting cap 15 and the securing cap are removed. It is clear that when the needle protecting cap 15 is removed, a tensile force is exerted on the active agent container 7 as a result of the static friction between the inner sleeve 17 and the active agent container 7. Consequently, the active agent container 7 must be prevented from leaving its position (e.g., being undesirably moved or pulled forward) in the auto-injector when the needle protecting cap 15 is removed.

For this purpose, a latching sleeve 20 is mounted in the front casing part such that it cannot move axially and at least one latching tongue 21 is arranged on the latching sleeve 20. Three latching tongues 21 are preferably provided in one embodiment, arranged or distributed symmetrically around the circumference of the latching sleeve. As FIG. 1 clearly shows, the free end of the latching tongue 21 abuts the flange 6 of the sliding sleeve 5 and thus prevents the sliding sleeve 5 from being pulled forwards together with the active agent container 7 arranged in it.

Figure 2:
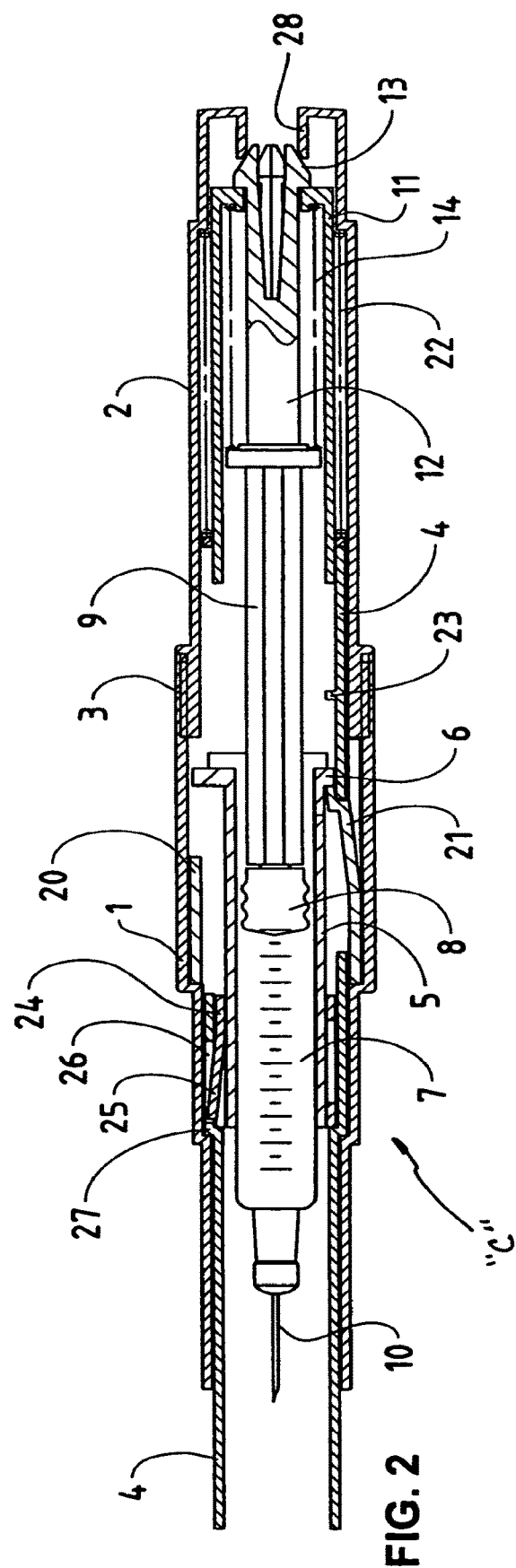
FIG. 2 depicts the state in which the auto-injector is unlocked.

FIG. 2 shows the auto-injector after the needle protecting cap 15 and the securing cap 18 have been removed as described above. The latching member 20 is still in the latching position and the latching tongue 21 prevents the active agent container 7, comprising or carrying the injection needle 10, from being slid forward. In addition, at the then open end, the needle protecting tube 4 creates a distance which prevents the injection needle 10 from being touched or at least makes it difficult to touch the injection needle 10. The needle protecting tube 4 is held in this position by the force of a spring 22 which is clamped between the rear end of the needle protecting tube 4 and the rear casing part 2.

FIG. 3 shows the auto-injector in a position which it assumes when it is pressed onto the skin of a patient but has not yet been triggered. The needle protecting tube 4 has been shifted backwards into the casing as compared to the position of FIG. 2, compressing the spring 22, such that the tip of the injection needle 10 is then situated slightly above the skin of the patient. FIG. 3 also shows that the needle protecting tube 4 shifted backwards has forced the latching tongue 21 outwards, which then exposes the flange 6 of the sliding sleeve 5. As compared to FIG. 2, it can be seen that a flange 23 formed internally in the rear part of the needle protecting tube 4 then abuts the front facing side of the guiding sleeve 11. It should be noted that the needle protecting tube still protrudes out of the front casing part 1 by a remaining amount at the front. However, as compared to FIGS. 1 and 2, it should be clear that the needle protecting tube 4 has slid the locking sleeve 24 some distance backward on the sliding sleeve 5.

FIG. 4 shows the auto-injector at the moment of triggering. Proceeding from the state depicted in FIG. 3, the user has pressed the auto-injector slightly harder onto the skin, such that the needle protecting tube 4 has been shifted into the casing by the remaining amount mentioned above, wherein the flange 23 has shifted the guiding sleeve 11 backwards in the rear casing part 2 by the remaining amount and the latching projections 13 have been moved into the region of a triggering ring 28 arranged in the rear end of the rear casing part 2. The triggering ring 28 has contacted and/or pressed the latching projections 13, formed on elastic arms of the driving part, far enough against each other that they are then pulled through the end opening of the guiding sleeve 11 by the force of the driving spring 14. The force of the driving spring 14 then acts, unobstructed, on the piston 8 via the piston rod 9, the piston 8 in practice abruptly increasing the hydraulic pressure in the active agent container 7. This pressure slides the active agent container forwards, such that the injection needle 10 penetrates into the skin of the patient. Since the diameter of the passageway in the injection needle 10 is comparatively small, at most a very small amount of the active agent can exit the injection needle 10 in this short period of time between triggering and the injection needle 10 penetrating into the skin.

The injection stroke is complete when the flange 6 of the sliding sleeve 5 abuts the end of the needle protecting tube 4 and/or the end of the locking sleeve 24. FIGS. 5 and 6 show the auto-injector in the position in which the injection needle 10 is inserted or injected, wherein FIG. 5 shows the operational state at the beginning of delivering the active agent and FIG. 6 shows the state of the auto-injector after the active agent container 7 has been completely emptied. When the operational state in accordance with FIG. 6 has been reached, the user retracts the auto-injector in order to remove the injection needle 10 from his skin.

FIG. 7 shows the operational state after the injection needle 10 has been removed from the skin of the patient. The needle protecting tube 4 was shifted back into its initial state by the force of the spring 22 as soon as the auto-injector was lifted from the skin of the patient. It then mainly serves to substantially cover the injection needle and protect the user and other persons from injuries from the injection needle 10. Consequently, the needle protecting tube 4 must be prevented from being shifted relative to the injection needle 10 such that the injection needle 10 protrudes out of the needle protecting tube 4. This task is accomplished by the locking tongue 25, which is formed in the locking sleeve 24. While the needle protecting tube 4, as mentioned, has been shifted forwards by the spring force, the locking sleeve 24 maintains its position on the sliding sleeve 5 as a result of a latch tongue 29 formed on the sliding sleeve 5, which then protrudes into a cavity of the locking sleeve 24 in the position in accordance with FIG. 7 and thus fixes it in place on the sliding sleeve 5.

As can clearly be seen in FIG. 7, the free end of the locking tongue 25 at the rear end of the needle protecting tube 4 then protrudes into its path. Thus, the needle protecting tube 4 cannot be retracted without the locking sleeve 24, the sliding sleeve 5 and the active agent container 7 together with the injection needle 10, being shifted backwards relative to the front casing part 1 and the rear casing part 2, against the force of the driving spring 14. Thus, the injection needle 10 maintains its relative position with respect to the needle protecting tube 4 and the injection needle 10 and is reliably prevented from being intentionally or unintentionally touched. This solution has the advantage that the axially directed force to be absorbed by the locking tongue 25 never exceeds the force of the driving spring 14, irrespective of how hard one presses against the front end of the needle protecting tube 4.

FIGS. 8 to 11 show another embodiment of an auto-injector in accordance with the present invention. In these figures, identical elements and elements having substantially the same function are denoted using the reference numerals from FIGS. 1 to 7. In this embodiment, the latching tongue 21 is guided by means of surfaces on the latching tongue 21 and the sliding sleeve 5, the surfaces running or extending obliquely with respect to the longitudinal axis of the auto-injector. The latching tongue 21 for latching the active agent container or the sliding sleeve 5 and the locking tongue 25 for latching the needle protecting tube 4 are also both arranged on the latching sleeve 20. In some preferred embodiments, the latching tongue 21 and the locking tongue 25 are formed integrally with the latching sleeve 20. In some embodiments, multiple latching tongues 21 and locking tongues 25 can be provided on the latching sleeve 20.

Figure 8:
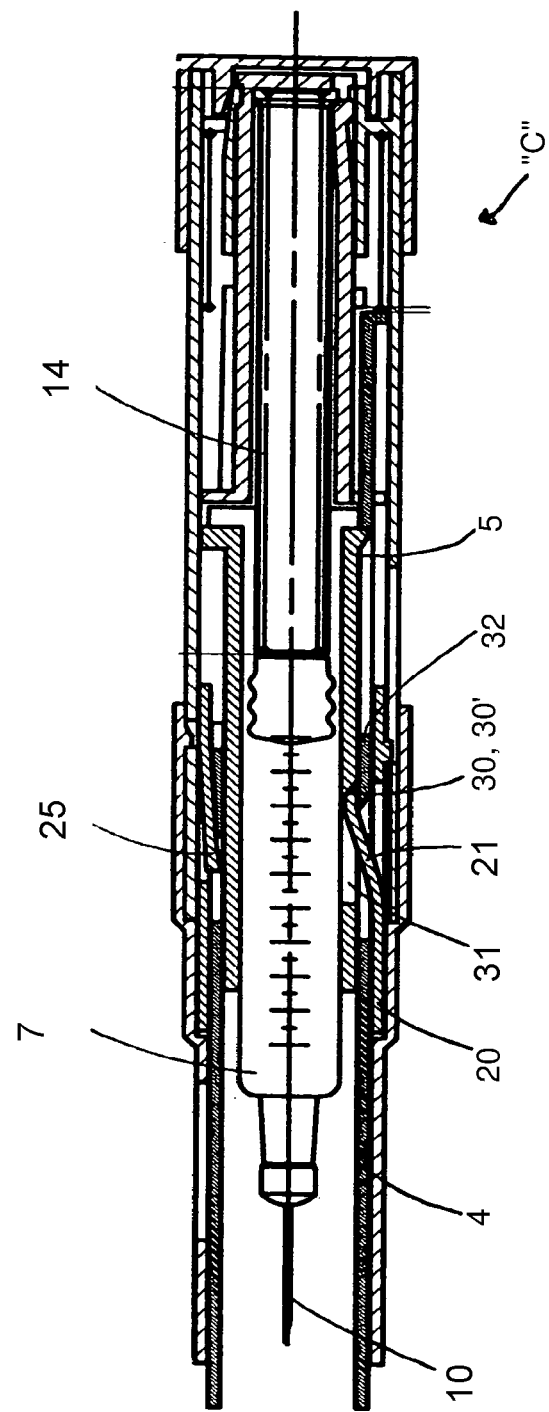
FIG. 8 depicts another embodiment of an auto-injector in accordance with the invention, in the latching position.

FIG. 8 shows a latching member in the form of a latching sleeve 20 which comprises a latching tongue 21 which comprises a surface 30 running or extending obliquely with respect to the longitudinal axis of the auto-injector, on its facing side. The tip of the oblique surface 30 abuts the outer side of the latching tongue 21. The sliding sleeve 5 comprises a cavity 31 into which the latching tongue 21 protrudes in the latching position. The edge of the cavity 31 opposite the oblique surface 30 of the latching tongue 21 comprises an oblique surface 30' which runs or extends generally parallel to the oblique surface 30 of the latching tongue 21. (In some embodiments, an oblique surface could be provided directly on the active agent container 7, such that the sliding sleeve 5 can be omitted.) The two oblique surfaces 30 and 30' come to rest on each other. The needle protecting tube 4 is at least partially arranged between the latching sleeve 20 and the sliding sleeve 5, wherein the latching tongue 21 protrudes through a cavity in the needle protecting tube 4 into the cavity 31 of the sliding sleeve 5. A part 32 of the needle protecting tube 4 overlaps the abutting point of the oblique surfaces 30 and 30', such that the latching tongue 21 is locked in the latching, latched or lacked position. In FIG. 8, a locking tongue 25 is also arranged on the sliding sleeve 5, on the side opposite the latching tongue 21. The locking tongue 25 protrudes into a cavity opposite it, in the needle protecting tube 4.

FIG. 9, generally analogous to FIG. 3, shows the auto-injector in a release position in which the needle protecting tube 4 is slid into the casing "C". In this position, the part 32 of the needle protecting tube 4 has been retracted from the overlapping area of the oblique surfaces 30 and 30'. The latching tongue 21 can then be moved into the cavity 31 of the needle protecting tube 4. The movement can be caused by a bias on the elastic latching tongue 21. In some preferred embodiments, however, the latching tongue 21 is slid outwards into the cavity by the pressure exerted by the driving spring 14, which acts on the oblique surface 30.

FIG. 10, generally analogous with FIG. 5, shows the auto-injector in a position in which the active agent container 7 is advanced relative to the casing "C" and the injection needle 10 is injected into a tissue. The sliding sleeve 5 has been advanced together with the active agent container 7 in a distal direction along the latching sleeve 20, wherein the latching tongue 21 comes to rest in the cavity 31 of the needle protecting tube 4.

Figure 11:
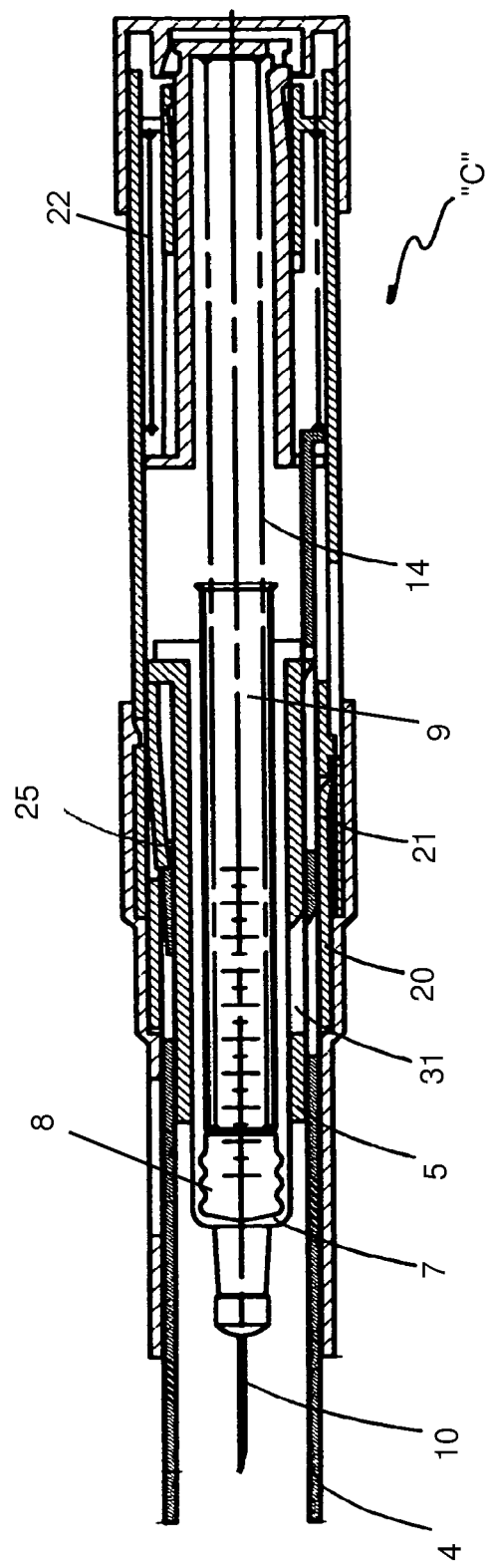
FIG. 11 depicts the auto-injector embodiment of FIG. 8 in a locking position in which the needle protecting tube is latched.

FIG. 11, generally analogous with FIG. 7, shows the auto-injector in a position in which the needle protecting tube 4 surrounds the injection needle 10 after the auto-injector has been removed from the surface of the tissue. In this embodiment, the locking tongue 25 is likewise arranged on the sliding sleeve 5. This enables a component to be omitted in the auto-injector. When the needle protecting tube 4 is advanced, the locking tongue 25 grips behind the end edge of the needle protecting tube 4, such that the needle protecting tube 4 is secured against retracting relative to the active agent container 7 or the sliding sleeve 5. When pressure is applied to the needle protecting tube 4 in the proximal direction, the needle protecting tube 4 shifted together with the sliding sleeve, the active agent container 7 and the injection needle 10, relative to the casing "C".

In the foregoing description, embodiments of the present invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to use the invention in various embodiments and with various modifications as are suited to a particular use contemplated. All such modifications and variations are within the scope of the invention as determined by the appended claims when interpreted in accordance with the breadth they are fairly, legally, and equitably entitled.

What is claimed is:

1. A non-refillable auto-injector for automatically injecting an active agent, comprising:
   a) an elongated casing, the casing comprising a front casing part and a rear casing part non-detachably connected by a fixed latching connection;
   b) an injection needle connected to an active agent container;
   c) a piston shiftable in the active agent container, by a driving spring of the auto-injector, to deliver the active agent;
   d) a needle protecting tube shiftable into the casing against a force of a compressible spring, wherein the auto-injector is prevented from being intentionally or unintentionally triggered until the needle protecting tube has been shifted into the casing; and
   e) a needle protecting cap for substantially sealing a needle end of the auto-injector prior to use, wherein the needle protecting cap is formed such that when attached to the auto-injector, the needle protecting cap prevents the needle protecting tube from being touched, and
   f) wherein a locking member is provided for latching the needle protecting tube and latches the needle protecting tube in a locked position in which the needle protecting tube substantially surrounds the injection needle after the auto-injector has been lifted from a point of injection such that the needle protecting tube is prevented from being shifted relative to the injection needle.

2. The non-refillable auto-injector as set forth in claim 1, wherein the needle protecting cap comprises an outer sleeve extending over a front end of the casing.

3. The non-refillable auto-injector as set forth in claim 1, wherein the auto-injector is a disposable auto-injector.

4. The non-refillable auto-injector as set forth in claim 1, wherein in a latching position, a latching member is capable of preventing the driving spring from delivering the active agent, and wherein the needle protecting tube is shiftable into the casing to cause the latching member to be moved to a released position in which a force of the driving spring may act unobstructed on a piston rod.

5. The non-refillable auto-injector as set forth in claim 1, wherein a latching member is forced out of a latching position by shifting the needle protecting tube into the casing.

6. The non-refillable auto-injector as set forth in claim 1, wherein the locking member is configured as a locking sleeve with at least one locking tongue protruding outwards from the locking sleeve, wherein when the auto-injector is lifted from the point of injection, the needle protecting tube is shifted back into an initial state by the force of the compressible spring and a free end of the at least one locking tongue grips behind an end edge of the needle protecting tube such that the needle protecting tube is secured against retracting relative to the active agent container and is locked in the locked position in which the needle protecting tube substantially surrounds the injection needle.

7. The non-refillable auto-injector as set forth in claim 6, wherein the end edge of the needle protecting tube is formed between a proximal end and a distal end of the needle protecting tube.

8. The non-refillable auto-injector as set forth in claim 1, wherein a driving part contacts a piston rod and is biased against the piston rod by the driving spring.

9. The non-refillable auto-injector as set forth in claim 1, wherein the locking member permanently latches the needle protecting tube in the locked position after the auto-injector has been lifted from the point of injection.

10. A non-refillable auto-injector for automatically injecting an active agent, comprising:
   a) an elongated casing;
   b) an injection needle connected to an active agent container;
   c) a piston shiftable in the active agent container, by a driving spring of the auto-injector, to deliver the active agent;
   d) a needle protecting tube shiftable into the casing against a force of a compressible spring, wherein the auto-injector is prevented from being intentionally or unintentionally triggered until the needle protecting tube has been shifted into the casing, and wherein the needle protecting tube is non-removably attached to the casing; and
   e) a needle protecting cap for substantially sealing a needle end of the auto-injector prior to use, wherein the needle protecting cap is formed such that when attached to the auto-injector, the needle protecting cap prevents the needle protecting tube from being touched, and f) wherein a locking member is provided for latching the needle protecting tube and latches the needle protecting tube in a locked position in which the needle protecting tube substantially surrounds the injection needle after the auto-injector has been lifted from a point of injection such that the needle protecting tube is prevented from being shifted relative to the injection needle.

11. The non-refillable auto-injector as set forth in claim 10, wherein the needle protecting tube comprises a heel, and wherein after the auto-injector has been lifted from the point of injection, the heel abuts with the casing to thereby prevent the needle protecting tube from being detached from the casing.

12. The non-refillable auto-injector as set forth in claim 10, wherein the needle protecting cap comprises an outer sleeve extending over a front end of the casing.

13. The non-refillable auto-injector as set forth in claim 10 or 12, wherein the auto-injector is a disposable auto-injector.

14. The non-refillable auto-injector as set forth in claim 10, wherein in a latching position, a latching member is capable of preventing the driving spring from delivering the active agent, and wherein the needle protecting tube is shiftable into the casing to cause the latching member to be moved to a released position in which a force of the driving spring may act unobstructed on a piston rod.

15. The non-refillable auto-injector as set forth in claim 10, wherein a latching member is forced out of a latching position by shifting the needle protecting tube into the casing.

16. The non-refillable auto-injector as set forth in claim 10, wherein the locking member is configured as a locking sleeve with at least one locking tongue protruding outwards from the locking sleeve, wherein when the auto-injector is lifted from the point of injection, the needle protecting tube is shifted back into an initial state by the force of the compressible spring and a free end of the at least one locking tongue grips behind an end edge of the needle protecting tube such that the needle protecting tube is secured against retracting relative to the active agent container and is locked in the locked position in which the needle protecting tube substantially surrounds the injection needle.

17. The non-refillable auto-injector as set forth in claim 16, wherein the end edge of the needle protecting tube is formed between a proximal end and a distal end of the needle protecting tube.

18. The non-refillable auto-injector as set forth in claim 10, wherein a driving part contacts a piston rod and is biased against the piston rod by the driving spring.

19. The non-refillable auto-injector as set forth in claim 10, wherein the locking member permanently latches the needle protecting tube in the locked position after the auto-injector has been lifted from the point of injection.

* * * * *